US00PP13392P2

(12) United States Plant Patent
Slaughter et al.

(10) Patent No.: US PP13,392 P2
(45) Date of Patent: Dec. 24, 2002

(54) PEACH TREE NAMED 'BURPEACHSIX'

(75) Inventors: John K. Slaughter, Clovis; Timothy J. Gerdts, Kingsbury, both of CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 09/479,687

(22) Filed: Jan. 7, 2000

(51) Int. Cl.[7] ..... A01H 5/00

(52) U.S. Cl. ..... Plt./198
(58) Field of Search ..... Plt./198

*Primary Examiner*—Bruce R. Campell
*Assistant Examiner*—Anne Marie Grünberg
(74) *Attorney, Agent, or Firm*—Wells St. John P.S.

(57) ABSTRACT

A new and distinct variety of peach tree denominated varietally as, Burpeachsix and which is characterized as to novelty by a date of maturity for commercial harvesting and shipment approximately June 18 to June 25 under the ecological conditions prevailing in the San Joaquin Valley of central California.

1 Drawing Sheet

BACKGROUND OF THE NEW VARIETY

The present invention relates to a new, novel and distinct variety of peach tree, *Prunus persica* which has been denominated varietally as 'Burpeachsix'. The 'Burpeachsix' Peach Tree produces an exceptionally high quality, peach which is mature for harvesting and shipment in the mid-season. Still further, another unique aspect of the 'Burpeachsix' is that it yields a very firm peach that has a high eating quality as compared with the other peach varieties which ripen at approximately the same time of the season.

ORIGIN OF THE NEW VARIETY

The present variety of peach tree resulted from an on-going program of fruit and nut tree breeding. The purpose of this program is to improve the commercial quality of deciduous fruit and nut varieties and rootstocks by creating and releasing promising selections of prunus, malus and regia species. To this end, we make both controlled and hybrid cross pollinations each year in order to produce seedling populations from which improved progenies are evaluated and selected. The seedling 'Burpeachsix' was originated by us in 1994, and was chosen from among a population of seedlings which resulted from a controlled cross pollination of the 'Grand Diamond' Nectarine Tree (U.S. Plant Pat. No. 4,095), which was used as the pollen parent, and the 'July Lady' Peach Tree (U.S. Plant Pat. No. 3,023), which was used as the seed parent. The resulting seed from this cross was planted in the spring of 1995. The new variety was selected from among seedlings growing in experimental orchards near the city of Fowler, Calif., County of Fresno, in the Central San Joaquin Valley. The Peach Tree 'Burpeachsix' was subsequently marked and noted as having exceptional characteristics. After the 1996 season, the Peach Tree 'Burpeachsix' was selected for advanced evaluation and repropagation. It has been subsequently evaluated during the 1996–1999 fruiting seasons.

ASEXUAL REPRODUCTION

Scionwood from the original seedling of the Peach Tree, 'Burpeachsix' was collected and grafted in the evaluation plot in the experimental orchard previously described onto two different and existing 'Nemared' (unpatented) rootstocks in February of 1997. The resulting propagation (fruit and scion) have been subsequently evaluated in the 1998 and 1999 seasons. These evaluations clearly demonstrated that the repropagated trees are true to the fruiting and vegetative characteristics of the original seedling in all observable aspects.

SUMMARY OF THE VARIETY

The 'Burpeachsix' Peach Tree is characterized as to novelty by producing fruit which have a mid-season ripening date, and which are further of high quality, firm, and have an attractive exterior coloration. In this regard, the present variety of peach tree bears freestone fruit which are ripe for commercial harvesting and shipment on approximately June 18 to June 25. These harvesting dates are approximately one week later then the harvesting dates of the commercial freestone peach variety 'Red Top' Peach Tree (U.S.D.A. nonpatented). The present variety distinguishes itself from the 'Red Top' Peach Tree, however, by producing fruit having a brighter and more extensive exterior coloration, and which has a firmer flesh. Further, the Burpeachsix Peach Tree distinguishes itself from the Red Top Peach Tree in that the fruit of the Burpeachsix Peach Tree has a keeping quality after it is harvested, that is superior in relative comparison to the fruit produced by the 'Red Top' Peach Tree.

BRIEF DESCRIPTION OF THE DRAWING

The accompanying drawing is a color photograph of a characteristic twig bearing typical leaves; several leaves showing both the dorsal and ventral coloration thereof; and several mature fruit displaying their external coloration sufficiently matured for harvesting and shipment. Additionally, one fruit of the subject variety is dissected in the equatorial or cheek plane to illustrate the flesh and stone characteristics thereof.

DETAILED DESCRIPTION

Referring more specifically to the pomological details of this new and distinct variety of peach tree, the following has been observed in 1999 under the ecological conditions prevailing at orchards located near the town of Fowler, county of Fresno, state of California. All major color code designations are by reference to The R.H.S. Colour Chart (1995 Third Edition) provided by The Royal Horticultural Society of Great Britain.

Tree:

*Size.*—Generally — Average to above average as compared to other common commercial peach cultivars. The age of the observed tree described in this specification was 5 years old.

*Productivity.*—Productive.

*Figure.*—The original seedling was trained in a central leader configuration with a moderate spread in the crown of the tree. The tree is considered upright to upright spreading in form.

*Height.*—The original seedling had a height dimension of 3.99 m at the end of the 1999 growing season.

*Width.*—The original seedling tree had an 2.46 m width at the end of the 1999 growing season.

*Current season growth.*—The current season growth for the new variety was approximately 0.94–1.18 m.

*Regularity of bearing.*—Regular, and considered hardy under typical central San Joaquin Valley climatic conditions.

Trunk:

*Diameter.*—Approximately 66.3 mm in diameter when measured at a distance of approximately 15.24 cm above the soil level, at the end of the 1999 growing season.

*Bark texture.*—Considered moderately rough with numerous folds of papery scarf skin being present.

*Lenticels.*—Numerous flat, oval lenticels are present. The lenticels range in size from approximately 3.0 to 7.0 millimeters in width, and from approximately 1 to 2 millimeters in height.

*Lenticel color.*—RHS Greyed-Orange Group 171 A.

*Bark coloration.*—Variable, but it is generally considered to be a grey-brown (RHS Greyed-Brown Group 174 A).

Branches:

*Size.*—Considered medium for the variety.

*Diameter.*—The branches have a diameter of generally, about 50.3 mm when measured during the third year after grafting.

*Surface texture.*—Average, and appearing furrowed on wood which is several years old.

*Crotch angles.*—Variable between about 42° to 48° from the horizontal axis for the scaffold limbs. This is not distinctive of the variety, however.

*Current season shoots.*—Surface Texture — Substantially glabrous.

*Internode length.*—Approximately 2.2 to 2.4 cm.

*Color of mature branches.*—Medium brown, RHS Grey Brown Group N 199 C.

*Current season shoots.*—Color — Light green, (RHS Yellow Green Group 144 C), with some reddish-brown coloration appearing on exposed exterior shoots (RHS Greyed Red Group 181 B). The color of the new shoot tips is considered a bright and shiny green (RHS Green Group 143 B).

Leaves:

*Size.*—Considered average for the species. Leaf measurements have been taken from vigorous upright current season growth taken approximately at mid-shoot.

*Leaf length.*—Approximately 165 to 175 millimeters.

*Leaf width.*—Approximately 49 to 51 millimeters.

*Leaf thickness.*—Approximately 1 to 2 millimeters.

*Leaf base shape.*—Slightly oblique.

*Leaf form.*—Lancelolate.

*Leaf tip form.*—Acuminate.

*Leaf color.*—Dark green, (RHS Green Group 137 C).

*Leaf texture.*—Glabrous.

*Lower surface color.*—Light green, (RHS Green Group 146 B).

*Venation.*—Pinnately veined.

*Mid-vein.*—Color — Light yellow green, (RHS Yellow Green Group 153 B).

*Leaf margins.*—Form — Considered crenate, occasionally doubly crenate. Uniformity — Considered generally uniform.

*Leaf petioles.*—Size — Considered medium for the species. Length — Approximately 6 to 9 millimeters. Diameter — Approximately 1.5 to 2 millimeters. Color — Pale green, (RHS Yellow Green Group 150 D).

*Leaf glands.*—Size — Approximately one to two millimeters in height and two to three millimeters in width. Numbers — Generally 1–2 per side, and generally located at the junction of the petiole and the leaf margin. Type — Reniform and small. Color — Greenish brown (RHS Grey Brown 199 C).

*Leaf stipules.*—Size — Approximately 11.0 mm in length; 1.0 mm in width. Number — Typically 2 per leaf bud and up to 6 per shoot tip. Length — Approximately 6 to 9 millimeters. Form — Lanceolate in form and having a serrated margin. Color —Green (RHS Green Group 132 A) when young but changing to a to yellow-brown color (RHS Grey Orange Brown 177 A) with advancing senescence. The stipules are considered to be early deciduous.

Flowers:

*Flower buds.*—Generally — The floral buds are considered to be small in size, 12.0 mm long and 6.0 mm wide, plump to slightly pointed in form, and slightly appressed, relative to the bearing shoot.

*Flower buds.*—Color — The bud scales are gray-brown, (approximately RHS Greyed Orange Group 177 B). The buds are considered hardy under typical central San Joaquin Valley climatic conditions.

*Hardiness.*—No winter injury has been noted during the several years of evaluation in the central San Joaquin Valley. The current variety has not been intentionally subjected to drought or heat stress and therefore this information is not available.

*Blooming time.*—Considered slightly earlier than average in relation to other peach cultivars commonly growing in the central San Joaquin Valley. Date of full bloom was observed on Mar. 8, 1998.

*Flower type.*—The variety is considered to be a non-showy type flower.

*Flower size.*—Flower diameter at full bloom is approximately 21 to 27 millimeters.

*Bloom quantity.*—Considered abundant.

*Flower bud frequency.*—Normally 1 to 2 buds appear per node, although 1 bud per node is more common.

*Petal size.*—Generally — Considered medium-large for the species. Lengh — Approximately 10 to 12 millimeters. Width — Approximately 7 to 9 millimeters.

*Petal form.*—Broadly ovate.

*Petal count.*—Nearly always 5.

*Petal texture.*—Glabrous.

*Petal color.*—Light pink when young, (approximately RHS Red Purple Group 68 B), and with advancing senescence changing to a very pale pink (RHS Red Purple Group 68 B). The lower portion of the flower petal has a color of RHS 68 B.

*Fragrance.*—Slight.

*Petal claw.*—Form — The claw is considered truncate in shape and has a small sized when compared to other similar varieties. Length — Approximately 1.5 to 2 millimeters. Width.— Approximately 1 millimeter.

*Petal margins.*—Generally — Considered variable, from nearly smooth, to moderately undulate.

*Petal apex.*—Generally — The petal apices appear slightly domed.

*Flower pedicel.*—Length — Considered medium-short, and having an average length of approximately 2.0 to 3.0 millimeters. Diameter — Considered average, approximately 2 millimeters. Color — Bright green (RHS Yellow Green Group 144 D).

*Floral nectaries.*—Color — Dull orange to an orange-gold color, (approximately RHS Greyed Orange Group 168 B). The color of the nectaries become increasingly dull and slightly darker with advancing senescence.

*Calyx.*—Surface texture — Generally glabrous, with slight ribbing occasionally being evident. Color — A dull red, (approximately RHS Greyed Red Group 184 A).

*Sepals.*—Surface Texture — The surface has a slight medium length, wooly, and gray colored pubescence. Size — Typically 4.0 mm wide; 6.0 mm long; and ovate in form. Color — A dull red (approximately RHS Greyed Red Group 178 A).

*Anthers.*—Generally — Average in size; approximately 17.0 mm in length and 1.0 mm in width. Color — Red to reddish-orange dorsally, (approximately RHS Greyed Purple Group 187 D). Pollen Production — Pollen is abundant, and has a yellow-orange color, (approximately RHS Yellow Orange 23B).

*Filaments.*—Size — Variable in length, approximately 14 to 16 millimeters. Color — White, (RHS Red Purple Group 69 D), and darkening with advanced maturity.

*Pistil.*—Generally — Average in size. Length — Approximately 15 to 17 millimeters, including the ovary. Color — Considered a very pale green, at midbloom, (approximately RHS Yellow Green Group 151 D), and becoming slightly more yellowish with advancing senescence. Surface Texture — Pubescent.

Fruit:

*Maturity when described.*—The present variety of fruit is described, as it would be found in its firm ripe condition at full commercial maturity. In this regard, the fruit of the present variety was first picked on approximately Jun. 18, 1998. The date of last pick of the same fruit in 1998 was approximately Jul. 25, 1998 under the ecological conditions prevailing in the San Joaquin Valley of Central California.

*Size.*—Generally — Medium in size, and considered moderately uniform.

*Average cheek diameter.*—Approximately 74 to 76 millimeters.

*Average suture diameter.*—Approximately 75 to 79 millimeters.

*Average axial diameter.*—Approximately 74 to 78 millimeters.

*Fruit form.*—Generally — Globose in its lateral aspect. The fruit is generally uniform in symmetry with a rounded and somewhat globose form when viewed from the apical aspect.

*Fruit suture.*—Generally — The suture appears as a thin line, which extends from the base to the apex and appears slightly deeper, basally, within the stem well, and apically on both sides of the pistil point. No apparent callousing or stitching exists along the suture line.

*Color.*—The suture normally is the same color as the underlying blush, both where the orange-yellow background color, (RHS Yellow Group 24 C) and the red orange color (RHS Red Group 46 A to 46 B) occur.

*Ventral surface.*—Form — Considered uniform.

*Stem cavity.*—Size — Considered moderate for the species. Width — Approximately 19–21 millimeters. Length — Approximately 27–30 millimeters. Depth — Approximately 10 to 11 millimeters. Form — Considered narrowly oval. Fruit Base — Generally — Considered truncate in form, and uniform. Fruit Apex — Generally — Considered depressed and usually recessed below the height of the apical shoulders.

*Fruit stem.*—Generally — Considered medium in length, approximately 9 to 10 millimeters. Diameter — Approximately 3 to 4 millimeters. Color — Generally a pale yellow-green (approximately RHS Yellow Green Group 145 B).

*Fruit skin.*—Generally — Considered average in thickness. Surface Texture — The variety has very short, fine pubescent surface. Skin Acidity — Considered neutral.

*Tenacious to flesh.*—Yes at commercial maturity.

*Tendency to crack.*—Not observed.

*Skin color.*—Generally — Variable, with approximately 70% to 80% of the fruit surface covered with a brilliant crimson red blush.

*Blush color.*—The blush color is generally more prevalent apically. This red blush color ranges from a dark red, (RHS Red Orange Group 45 A and B) to an orange red, (RHS 51 A), with many degrees of shading and blending between these colorations.

*Skin ground color.*—This is generally present in variable percentages covering approximately 10% to 20% of the fruit's surface, and which is a Yellow-golden color (RHS Yellow Orange Group 22 A to 24 C).

*Flesh color.*—Generally — Considered variable from a yellow/orange color, (RHS Yellow Orange Group 20 B to 21 A).

*Flesh fibers.*—Generally — Present, numerous, fine and light colored. These fibers are present throughout the flesh.

*Stone cavity.*—Color — Bright pink, (approximately RHS Red Orange Group 52 A), to a yellow orange color, (approximately RHS Yellow Group 18 B).

*Flesh texture.*—Generally — The flesh is considered firm and fine at full commercial maturity. The flesh is considered firm yet melting.

*Ripening.*—Generally — The fruit of the present variety ripens evenly.

*Flavor.*—Considered sweet and having moderate acidity. The flavor is considered both pleasant and well balanced.

*Aroma.*—Pleasant and abundant.

*Eating quality.*—Generally — Considered good to well above average when compared to other common peach tree varieties which ripen in the same season.

Stone:

*Attachmemt.*—Generally — The stone is considered a freestone. A little air space at the cavity margin is normally evident.

*Stone size.*—Generally — Considered medium large for the species.

*Length.*—Approximately 32 to 35 millimeters.

*Width.*—Approximately 27 to 30 millimeters.

*Diameter.*—Approximately 21 to 23 millimeters.

*Fibers.*—Generally — A few medium length fibers are attached along the entire surface of the stone.

*Stone form.*—Generally — The stone is considered rounded to slightly oval.

*Stone base.*—The stone base is generally considered truncate.

*Base angle.*—The base angle of the stone is variable, but generally is considered oblique to the stone axis.

*Hilum.*—Generally — Considered medium in size, and moderately well defined. The hilum is approximately 5 to 7 millimeters long, and approximately 3 to 4 millimeters wide. Form — Considered oval.

*Apex.*—Shape — The stone apex is raised and has an acute tip.

*Stone shape.*—Considered variable. The stone is normally equal, although occasionally it may appear nearly unequal.

*Stone surface.*—Surface Texture — Generally considered medium in roughness, and exhibits substantial pitting laterally. Substantial grooving is apparent over the apical shoulders. Surface pitting is prominent, generally. Ridges — Numerous fine ridges are present basally, and converge towards the base of the stone.

*Ventral edge.*—Width — Considered medium, and prominent, and having a dimension of approximately 4 to 6 millimeters at mid-suture. The wings are most prominent over the basal area.

*Dorsal edge.*—Full, heavily grooved and having jagged edges. The dorsal edge is moderately eroded over the apical shoulder.

*Stone color.*—The color of the dry stone is approximately a light to medium brown, (RHS Orange Red Group 34 C).

*Tendency to split.*—No splitting noted.

Kernal:

*Form.*—Oval when fruit is ripe.

*Length.*—About 17–19 mm.

*Width.*—About 10–12 mm.

*Thickness.*—About 3–4 mm.

*Pellicle.*—Slight pubescence is observed.

*Color.*—(RHS Greyed-Orange Group 175 C).

*Use.*—The subject variety Burpeachsix is considered to be a peach of mid-season maturity, with a very firm flesh, highly attractive exterior color, and which is useful for both local, and long distance shipping.

*Keeping quality.*—Excellent. Fruit has stored well up to 18 days after harvest at temperatures of about 1° C.

*Resistance to insects and disease.*—No particular susceptibilities were noted.

*Shipping quality.*—Well above average.

Although this new variety of peach tree possesses the described characteristics noted above, as a result of the growing conditions prevailing in the central part of the San Joaquin Valley of California, it is to be understood that variations of the usual magnitude and characteristics incident to changes in growing conditions, fertilization, pruning, and pest control are to be expected.

Having thus described and illustrated our new Peach tree variety, what we claim is new and desire to secure by Plant Letters Patent is:

1. A new and distinct variety of peach tree substantially as illustrated and described and which is characterized as to novelty by producing an attractively colored freestone peach which is sufficiently matured for harvesting and shipment approximately June 18 to June 25 under the ecological conditions prevailing in the San Joaquin Valley of central California.

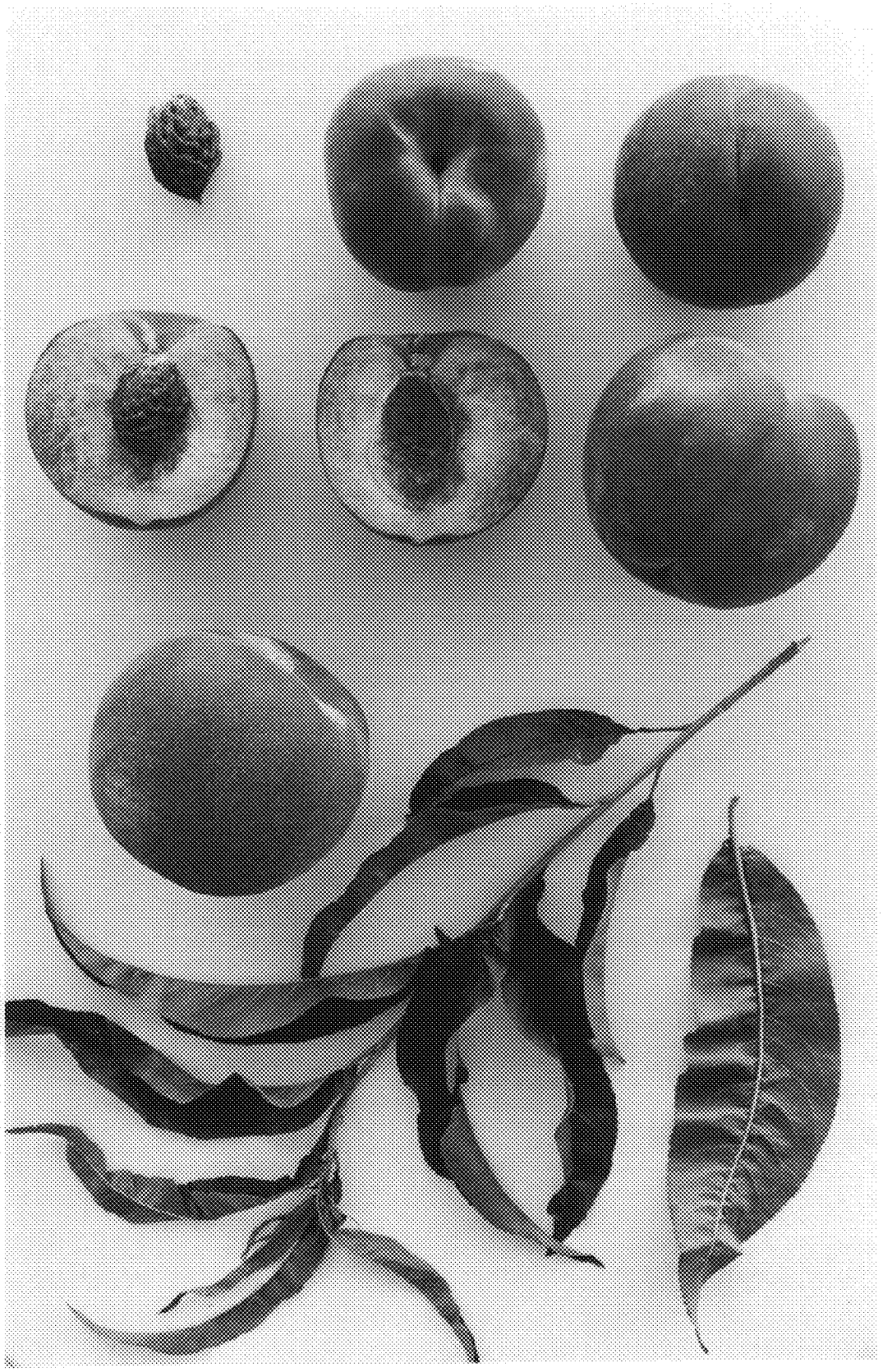

* * * * *